United States Patent [19]
Fujisawa et al.
[11] Patent Number: 5,028,524
[45] Date of Patent: Jul. 2, 1991

[54] ASSAY FOR ANTI-PRE-S ANTIBODY

[75] Inventors: Yukio Fujisawa, Kobe; Osamu Nishimura, Kawanishi; Yasuaki Itoh, Tsukuba, all of Japan

[73] Assignee: Takeda Chemical Industries, Ltd., Osaka, Japan

[21] Appl. No.: 181,210

[22] Filed: Apr. 13, 1988

[30] Foreign Application Priority Data

Apr. 24, 1987 [JP] Japan ............................... 62-102950

[51] Int. Cl.[5] ..................... C12Q 1/70; G01N 33/546; C07K 7/00

[52] U.S. Cl. ........................................ 435/5; 436/533; 436/534; 436/820; 436/828; 530/324

[58] Field of Search .................... 435/5; 436/820, 533, 436/534, 828; 530/324

[56] References Cited

U.S. PATENT DOCUMENTS 4,228,237 10/1980 Hevey et al. .......................... 435/7
4,591,552 5/1986 Neurath ............................. 436/534

FOREIGN PATENT DOCUMENTS 0154902 2/1985 European Pat. Off. .
0160900 4/1985 European Pat. Off. .
2026691 7/1979 United Kingdom .

OTHER PUBLICATIONS

Neurath et al., Nature, 315: 154–156, "Hepatitis B Virus Contains Pre-S Gene Encoded Domains", May 9, 1985.
Neurath et al., Cell, 46: 429–436, "Identification and Chemical Synthesis of a Host Cell Receptor Binding Site on Hepatitis B Virus", Aug. 1, 1986.
Tijssen, *Laboratory Techniques in Biochemistry and Molecular Biology*, vol. 5, "Practice and Theory of Enzyme Immunoassays", Elsevier, N.Y., 1–37 (1985).
Okamoto, H. et al., 1986, Nucleotide Sequence of Cloned Hepatitis B Virus Genome, Subtype Ayr: . . . J. Gen. Virol. 67 2305.
Neurath, A. R. et al., Molecular Immun., vol. 24, No. 6: 561–568 (1987).
Neurath, A. R. et al., Advances in Virus Res., vol. 34:66–142 (1988).
Guesdon et al., Journ. of Histochem. & Cytochem. 27:8, pp. 1131–1139.
Okamoto et al., Hepatology, 6:3, pp. 354–359 (1986).
Budkowsak et al., Hepatology, 6:3, pp. 360–368 (1986).
Itoh, Y. et al., Proc. Natl. Acad. Sci: U.S.A., 83, pp. 9174–9178 (1986).

*Primary Examiner*—Robert J. Warden
*Assistant Examiner*—John Groelke
*Attorney, Agent, or Firm*—David G. Conlin; Ronald I. Eisenstein

[57] ABSTRACT

Assays for an anti-pre-S antibody in a human serum by an enzyme immunoassay in which a biotin-avidin system is used are disclosed. The assays include inhibition method, sandwich method, competitive method and Protein A or anti-human IgG antibody method in a solid phase.

The assays can determine the anti-pre-S antibody titer in human sera highly sensitively and simply without use of radioactive materials.

12 Claims, 1 Drawing Sheet

Biotinated pre-S peptide, Avidinated HRP, Specimen,
37°C, 3 hr.
Anti-pre-S antibody
37°C, 3 hr.
Washing
Substrate solution Room temperature 30 min.
2N $H_2SO_4$
$A_{492}$ measurement 1-1

Specimen
Pre-S peptide-Thyroglobulin Conjugate
Room temperature, Overnight
Washing
Biotinated pre-S peptide, Avidinated HRP 37°C, 2 hr.
Washing
Substrate solution Room temperature, 30 min.
2N $H_2SO_4$
$A_{492}$ measurement 1-2

Specimen
Protein A or Anti-human IgG antibody
Room temperature, Overnight
Washing
Biotinated pre-S peptide, Avidinated HRP 37°C, 2 hr.
Washing
Substrate Solution Room temperature, 30 min.
2N $H_2SO_4$
$A_{492}$ measurement 1-3

Biotinated pre-S peptide, Avidinated HRP, Specimen,
Pre-S peptide-Thyroglobulin Conjugate
37°C, 3 hr.
Washing
Substrate Room temperature 30 min.
2N $H_2SO_4$
$A_{492}$ measurement 1-4

ASSAY FOR ANTI-PRE-S ANTIBODY

FIELD OF THE INVENTION

The present invention relates to an assay for an anti-pre-S antibody in a human serum, more particularly to a method for determining an antibody to the pre-S region present at the N-terminal of the L-protein or the M-protein in hepatitis B virus (HBV) env proteins by an enzyme immunoassay in which a biotin-avidin system is used.

DESCRIPTION OF THE PRIOR ART

It has been known that the pre-S antigen-anti-pre-S antibody system is induced in the sera of patients with acute hepatitis infected with HBV and developing the symptoms thereof, prior to the induction of the HBs antigen-anti-HBs antibody system, the HBc antigen-anti-HBc antibody system and the HBe antigen-anti-HBe antibody system [A. Robert Neurath, et al., Nature, 315, 154 (1985)]. It has been noted what kind of role is played by the pre-S antigen and the anti-pre-S antibody in respect to the completion of HBV infection, the mechanism by which the symptoms of type B hepatitis are developed, and the prevention thereof and the like. Particularly, it has recently been proven by experiments conducted by use of chimpanzees that antisera to a pre-S2 peptide in the pre-S region neutralize HBV [A. Robert Neurath et al., Vaccine, 4, 35 (1986)] and the development of the symptoms of acute hepatitis caused by HBV is prevented by a pre-S2 peptide vaccine [Y. Itoh et al., Proc. Natl. Acad. Sci. U.S.A., 83, 9174 (1986)]. It has further been reported that antibodies to a pre-Sl peptide in the pre-S region prevent the binding of HBV to cells derived from hepatoma [A. Robert Neurath et al., Cell, 46, 429 (1986)]. As the importance of anti-S antibody is thus recognized, there has been desired to develop a system by which anti-pre-S antibody in sera of hepatitis B patients or persons inoculated with the hepatitis B vaccine can be determined specifically and sensitively.

When the antibodies in human sera are determined by the usual enzyme immunoassay (EIA), a remarkably unspecific reaction is often observed, greatly different from the case where sera of experimental animals are used. Therefore, highly diluted sera are necessary to be used. For this reason, the advantage of the enzyme immunoassay that it has high sensitivity can usually not be utilized. Consequently, when a low level of antibody titer in human sera is measured, the radioimmunoassay is employed in which an antigen or an antibody labeled with a radioactive material is used. Actually, the determination of human anti-pre-S antibody is also made by the radioimmunoassay. For example, an anti-pre-S antibody in sera of patients with acute type B hepatitis has been determined by detecting the antibody bound to a pre-S peptide in a solid phase by the antiglobulin method [A. Robert Neurath et al., Nature, 315, 154 (1985)]. The anti-pre-S antibody in human sera has been determined by the inhibition method by allowing human sera to react with an HBs antigen solution containing a definite amount of pre-S antigen, then binding the unreacted pre-S antigen-containing HBs antigen to beads coated with an anti-pre-S antibody, and detecting it by $^{125}$I-labeled anti-HBs antibody [A. Budkowska et al., Hepatology, 6, 360 (1986)]. Further, with respect to the human antibody to the polymerized albumin receptor (PAR) in the pre-S2 region, the anti-PAR antibody has been determined by the inhibition method by allowing sera to react with PAR-containing HBs particles in a solid phase, then binding polymerized human serum albumin (poly-HSA) to the unreacted PAR, and detecting it by $^{125}$I-labeled monoclonal anti-poly-HSA antibody [H. Okamoto et al., Hepatology, 6, 354 (1986)].

Thus, the radioimmunoassay is the only method known as a system for assaying sensitively the anti-pre S antibody in human sera. However, the use of radioactive materials for determination of antibody titer has many restrictions from the viewpoint of safety and operability. Therefore, the development of a highly sensitive determination system using non-radioactive materials has been awaited.

SUMMARY OF THE INVENTION

With this background, the present inventors undertook to develop a system by which anti-pre-S antibody in human sera can be determined highly senstively and simply without the use of radioactive materials.

As the assay for determining the antibody titer highly sensitively without use of radioactive materials, there are mentioned the enzyme immunoassay (EIA) and the enzyme linked immunosorbent assay (ELISA). When the anti-pre-S antibody in human sera is detected by the conventional EIA or ELISA, unspecific reactions are observed. In order to prevent them, sera diluted 100 to 400 times are necessary to be used. In contrast, the present inventors have found that the unspecific reactions can be repressed and the anti-pre-S antibody can be sensitively determined, when the antibody in human sera is determined by the EIA or ELISA using a biotin-avidin system (BAS), thus completing the present invention.

According to the present invention, there are provided (1) an assay for an anti-pre-S antibody in a human serum which comprises reacting a human serum specimen, a biotinated pre-S peptide and an avidinated enzyme with an anti-pre-S antibody bound to a carrier, and measuring enzyme activity on the carrier (Inhibition method), (2) an assay for an anti-pre-S antibody in a human serum which comprises reacting a human serum specimen with a pre-S peptide bound to a carrier, then adding a biotinated pre-S peptide and an avidinated enzyme thereto, and measuring enzyme activity on the carrier (Sandwich method), (3) an assay for an anti-pre-S antibody in a human serum which comprises reacting a human serum specimen, a biotinated anti-pre-S antibody and an avidinated enzyme with a pre-S peptide bound to a carrier, and measuring enzyme activity on the carrier (competitive method) and (4) an assay for an anti-pre-S antibody in a human serum which comprises reacting a human serum specimen, a biotinated pre-S peptide and an advidinated enzyme with an anti-human immunoglobulin G antibody or Protein A bound to a carrier, and measuring enzyme activity on the carrier (Protein A or anti-human IgG antibody solid-phase method).

DESCRIPTION OF THE PREFERRED EMBODIMENTS

Figure 1:
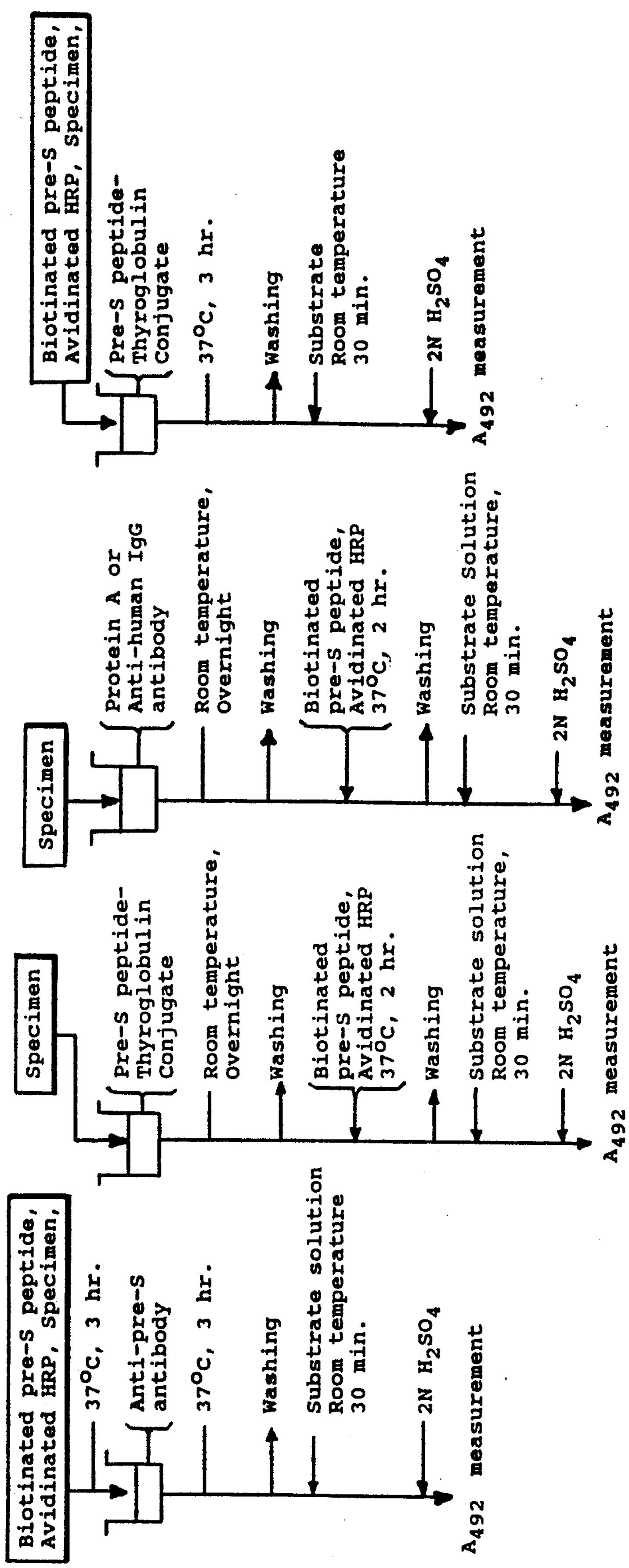
FIG. 1 shows the procedures for an assay for anti-pre-S antibodies. (1), (2), (3) and (4) show the assay procedures by the inhibition method, the sandwich method, the Protein A or anti-human IgG antibody method in solid phase and the competitive method, respectively.

As the above pre-S peptide, peptides containing a conserved region in the pre-S region among HBV subtypes such as adr, adw, ayw and ayr are suitable. There are preferably used a peptide comprising the following amino acid sequence from 21st to 47th in the pre-Sl region:

$PLGFX^1PDHQLDPAFX^2ANX^3X^4NPDWDFNP$ wherein $X^1$ represents F or L, $X^2$ represents G or R, $X^3$ represents S or T and $X^4$ represents N, T or A; a peptide comprising the following amino acid sequence from 25th to 42nd in the pre-S1 region:

$X^1PDHQLDPAFX^2ANX^3X^4NPD$ wherein $X^1$, $X^2$, $X^3$ and $X^4$ have the same meanings as defined above;

a peptide comprising the following amino acid sequence from 8th to 34th in the pre-S2 region:

$X^5HQX^6LX^7DPRVRGLYX^8PAGGSSSGTVNP$ wherein $X^5$ represents F, L or P, $X^6$ represents A or T, $X^7$ represents L or Q and $X^8$ represents F or L; and a conjugate of one or more of these peptides with a carrier protein such as bovine serum albumin, thyroglobulin and keyhole limpet hemocyanin. A polypeptide containing the above pre-S1 and/or pre-S2 may also be used. The pre-Sl peptide, the pre-S2 peptide and the polypeptide containing pre-S1 and pre-S2 can be synthesized by chemical syntheses or gene engineering procedures.

The anti-pre-S antibody can be obtained by inoculating an antigen containing a pre-S antigenic determinant an animal such as a rabbit, a horse or a bovine, and preparing the antibody from animal serum in which the antibody has been induced. The inoculation of the antigen in an animal to induce the antibody, the preparation of the serum and the preparation of the antibody from the serum can be performed by known methods. As the antigen containing the pre-S antigenic determinant, the above pre-S1 peptide, pre-S2 peptide or conjugates of carrier proteins and the above peptides may be used. There can be also used pre-S-containing antigens prepared by gene engineering procedures [M. L. Michel et al. Proc. Natl. Acad. Sci. U.S.A. 81, 7708 (1984); Y. Fujisawa et al. Gene, 40, 23 (1985); Y. Itoh and Y. Fujisawa, Biochem. Biophys. Res. Commun. 141, 942 (1986); P. Dehoux et al. Gene, 48, 155 (1986); the specification and figures of Japanese Patent Application No. 193833/86]. The biotinated pre-S peptide and the biotinated anti-pre-S antibody can be easily prepared by reacting the above pre-S peptide or anti-pre-S antibody with a biotinating agent such as NHS-biotin (biotinyl-N-hydroxy succinimide), sulfo-NHS-biotin or NHS-iminobiotin (Vector Laboratories, Inc.).

As the carrier, there can be mentioned particles and microplates of, for example, polystyrene, polycarbonate and agarose (Sepharose). The binding of the pre-S peptide, the anti-pre-S antibody, Protein A or the anti-human IgG antibody to the carrier is performed by contacting an aqueous solution or a buffer containing the peptide, antibody or Protein A described above with the carrier.

As Protein A, the anti-human IgG antibody and the avidinated enzyme, commercially available products may be employed respectively. The avidinated enzyme includes, for example, horseradish peroxidase avidin D, alkaline phosphatase avidin D, beta galactosidase avidin D and glucose oxidase avidin D (Vector Laboratories, Inc.).

The procedures of the assay for anti-pre-S antibody according to the present invention will hereinafter be described.

(I) INHIBITION METHOD

Step 1

A mixture of a human serum specimen (or a diluted solution thereof), a biotinated pre-S peptide and an avidinated enzyme is reacted with an anti-pre-S antibody bound to a carrier.

If an anti-pre-S antibody is not present in the serum specimen, a complex of carrier-anti-pre-S antibody-biotinated pre-S peptide-avidinated enzyme is formed. If an anti-pre-S antibody is present in the serum specimen, the biotinated pre-S peptide is first reacted with the anti-pre-S antibody in the serum specimen to reduce the formation of the complex on the carrier described above.

After the serum specimen (or the diluted solution thereof) is mixed with the biotinated pre-S peptide, the mixture may be reacted with the anti-pre-S antibody bound to the carrier and the avidinated enzyme.

The serum used is prepared from blood collected by a usual method. Also, the IgG fraction prepared from the serum may be used. The mixture of the serum, the biotinated pre-S peptide and the avidinated enzyme is usually allowed to stand or stirred at 4° to 45° C. for 1 to 20 hours. The reaction conditions of the mixture and the anti-pre-S antibody bound to the carrier are similar to those described above.

Step 2

The carrier is separated from the reaction mixture, and the enzyme bound to the carrier is reacted with a substrate.

The separation of the carrier from the reaction mixture is easily carried out by filtration or centrifugation when the carrier is a particle, or by washing away the reaction mixture with the washing when the carrier is a plate. The carrier is thereafter washed to remove the free avidinated enzyme or biotinated pre-S peptide, the biotinated pre-S peptide reacted with the anti-pre-S antibody in the serum and the avidinated enzyme. As the washing agent, there are used water, a sodium chloride solution and a phosphate buffer, each of which does not influence enzyme activity.

As the enzyme substrate, there can be mentioned the following:

A. Horseradish peroxidase (1) 5-Aminosalicylic acid-$H_2O_2$ pH at the reaction: 5.6

Assay: absorptiometry ($A_{450}$)

(2) o-Phenylenediamine-$H_2O_2$ pH at the reaction: 4.0

Assay: absorptiometry ($A_{492}$)

(3) Tyramine-$H_2O_2$ pH at the reaction: 8

Assay: fluorophotometry ($\lambda_{ex}$ 320 nm; $\lambda_{em}$ 450 nm)

(4) ABTS [2,2'-azinodi(3-ethylbensthiazoline)-6'-sulfonic acid]-$H_2O_2$ pH at the reaction: 4.0
Assay: absorptiometry ($A_{405}$, $A_{578}$)
B. Alkaline phosphatase
(1) p-Nitrophenol phosphoric acid
pH at the reaction: 8.2
Assay: absorptiometry ($A_{410}$)
(2) Phenylphosphoric acid-4-aminoantipyrine
pH at the reaction: 10.5
Assay: absorptiometry ($A_{500}$)
C. Beta galactosidase
(1) o-Nitrophenol-β-D-galactoside
pH at the reaction: 7.8
Assay: absorptiometry ($A_{420}$)
(2) 4-Methylumbelliferyl-β-D-galactoside
pH at the reaction: 7.8
Assay: fluorophotometry ($\lambda_{ex}$ 330 nm; $\lambda_{em}$ 453 nm: pH at the assay is 10.3)
D. Glucose oxidase
(1) Glucose Glucose is used as a substrate, and the formed $H_2O_2$ is allowed to luminesce by luminol-peroxidase (pH 8.5) and determined by the chemiluminescence method.

Each of the methods for assaying enzyme activity described above can be performed according to known methods. As a reaction terminating agent, there is used sodium azide, sulfuric acid or the like.

(II) Sandwich method

Step 1

A human serum specimen (or a diluted solution thereof) is reacted with a pre-S peptide bound to a carrier.

If an anti-pre-S antibody is present in the serum, a complex of the pre-S peptide and the anti-pre-S antibody is formed on the carrier. The reaction is usually conducted at 4° to 45° C. for 1 to 20 hours.

Step 2

A biotinated pre-S peptide and an avidinated enzyme are added to the reaction mixture of Step 1.

If an anti-pre-S antibody is present in the serum, a complex, carrier-pre-S peptide-anti-pre-S antibody-biotinated pre-S peptide-avidinated enzyme, is formed. The reaction is usually conducted at 4° to 45° C. for 1 to 20 hours.

Step 3

The carrier is separated from the reaction solution, and the enzyme bound on the carrier is reacted with the substrate.

This step is performed in the same manner as Step 2 in the inhibition method.

(III) Competitive method

Step 1

A mixture of a human serum specimen (or a diluted solution thereof), a biotinated anti-pre-S antibody and an avidinated enzyme is reacted with a pre-S peptide bound to a carrier.

In this reaction, when an anti-pre-S antibody is present in the serum specimen, the anti-pre-S antibody in the serum and the biotinated anti-pre-S antibody react competitively with the pre-S peptide bound to the carrier to form a complex of the carrier-pre-S peptide-anti-pre-S antibody, as well as a complex of the carrier-pre-S peptide-biotinated anti-pre-S antibody-avidinated enzyme.

The more anti-pre-S antibody in the serum is present, the less enzyme binds to the carrier. The reaction is usually conducted at 4° to 45° C. for 1 to 20 hours.

Step 2

The carrier is separated from the reaction mixture, and the enzyme bound on the carrier is reacted with the substrate.

This step is performed in the same manner as Step 2 in the inhibition method.

(IV) Protein A or anti-human IgG antibody method in a solid phase

Step 1

A mixture of a human serum specimen (or a diluted solution thereof), a biotinated pre-S peptide and an avidinated enzyme is reacted with an anti-human IgG antibody or Protein A bound to a carrier.

In this reaction, the anti-human IgG antibody or Protein A reacts with IgG in the serum. If an anti-pre-S antibody is present in the serum, the anti-pre-S antibody further reacts with the biotinated pre-S peptide and the avidinated enzyme to form a complex of the carrier-anti-human IgG antibody or (Protein A) -anti-pre-S antibody-biotinated pre-S peptide-avidinated enzyme. The reaction is conducted at 4° to 45° C. for 1 to 20 hours.

Step 2

The carrier is separated from the reaction mixture, and the enzyme bound on the carrier is reacted with a substrate.

This step is performed in the same manner as Step 2 in the inhibition method.

In the inhibition method, a normal human serum as a control is treated with the same procedure to determine its enzyme activity, and the activity is taken as 100%, and the anti-pre-S antibody titer is expressed as the maximum dilution of the human serum specimen which represses the resulting activity to 50%. Also, the activity of the human serum specimen compared with the control described above can be represented(inhibition ratio). The inhibition method is suitable for determining a low level of human anti-pre-S antibody titer, because of its high sensitivity. The three methods other than the inhibition method can be used for determining a relatively high level of human anti-pre-S antibody titer.

In the sandwich method and the Protein A or anti-human IgG antibody method in a solid phase, some sera each containing a human anti-pre-S antibody of a different concentration are manipulated in a similar manner as above to measuring the enzyme activity, and thereby the amount of the anti-pre-S antibody in the serum can be determined.

In the competitive method, the anti-pre-S antibody titer can be determined similarly to that of the inhibition method.

According to the present invention, anti-pre-S antibodies in human serum specimens can be determined simply and highly sensitively.

When amino acids are indicated by the abbreviations given in a single letter in this specification, the conventional abbreviations in the art are used and some examples are as follows. The amino acids represent the L-forms, unless otherwise specified.

A: Alanine
C: Cysteine

D: Aspartic acid
E: Glutamic acid
F: Phenylalanine
G: Glycine
H: Histidine
I: Isoleucine
K: Lysine
L: Leucine
M: Methionine
N: Asparagine
P: Proline
Q: Glutamine
R: Arginine
S: Serine
T: Threonine
V: Valine
W: Tryptophan
Y: Tyrosine The present invention will hereinafter be described in detail with the following Reference Examples and Examples. It is understood that these examples are not intended to limit the scope of the invention.

REFERENCE EXAMPLE 1

Synthesis of Pre-S2 Peptide, FHQALLDPRVRGLYFPAGGSSSGTVNP

The pre-S2 peptide described above was synthesized by the solid phase method by using a Model 430A Peptide Synthesizer (Applied Biosystems Inc., U.S.A.).

Starting from 600 mg of a Boc. Pro. Pam resin (Pam: 4-oxymethylphenylacetamide), the reaction was conducted according to the program to obtain 2.5 g of a peptide resin. Then, 612 mg of the resin thus obtained was treated with 6 ml of anhydrous hydrogen fluoride in the presence of 0.6 ml of anisole at 0° C. for 1 hour. The resulting free peptide was purified by using a PD-10 column (Pharmacia Inc., Sweden), Amberite IRA-400 (acetate form)(Rohm & Haas Inc., U.S.A.), and then a reversed phase high performance liquid chromatography A347-7 (S-70DS) YMC (Yamamura Chemical Co.). The yield was 50 mg.

Analytical amino acid values of the acid-hydrolysate (6N HCl, 110° C., 24 hours) were as follows:

Asp, 1.9 (2); Thr, 0.9 (1); Ser, 2.7 (3); Glu, 1.1 (1); Gly, 4.3 (4); Ala, 2.2 (2); Val, 2.1 (2): Leu, 3.0 (3); Tyr, 1.1 (1); Phe, 2.0 (2); His, 1.0 (1); Arg, 2.0 (2); and Pro, 2.8 (3). Recovery 78.9%. The theoretical values were designated in parentheses.

$[\alpha]_D^{25}-69.8$ (c=0.1, in 5% acetic acid)

REFERENCE EXAMPLE 2

Synthesis of Pre-S1 Peptide, PLGFFPDHQLDPAFGANSNNPDWDFNP

The pre-S1 peptide described above was prepared in a similar manner as described in Reference Example 1.

EXAMPLE 1

Assay for Anti-Pre-S2 Antibody by Inhibition Method i) Preparation of Anti-Pre-S2 Antibody

Purified modified P31 (M-P31c) particles described in Example 19 of the specification of Japanese Patent Application No. 61-193833 (1986) were inoculated in rabbits to obtain sera having a high antibody titer to the pre-S2 region. In three rabbits (Japanese White species, male, 3 kg), 100 μg per rabbit of the purified modified P31 (M-P31c) particles was subcutaneously inoculated at their back with Freund's complete adjuvant (DIFCO Inc.). At an interval of 2 weeks, the supplementary immunization was similarly carried out two times. After 1 week from the third immunization, 50 ml of blood was collected from the auricular vein to obtain about 25 ml of serum. To 10 ml of the serum, 6.7 ml of a saturated ammonium sulfate solution was added, and the mixture was allowed to stand at room temperature for 1 hour with stirring. Then, after centrifugation (10000 g, 10 minutes), a precipitate was collected. The precipitate was dissolved in 2 ml of distilled water and dialyzed against 15 mM sodium phosphate buffer (pH 6.3). Subsequently, the dialized solution was fractionated by a DEAE-cellulose column (1.6 cm×12 cm) equilibrated with the same buffer as above, and immunoglobulin G (IgG) eluting out without being adsorbed was collected, to obtain 71 mg of IgG. The IgG contained a large amount of antibody to the M-P31c particles, and was particularly rich in anti-pre-S2 antibody.

ii) Preparation of Solid Phase

100 μl of the above antibody solution [IgG 20 μg, 0.1 M sodium carbonate buffer (pH 9.6)] was dividedly poured into each well of a microtiter plate (Nunc Inc. Immunoplate type I), and allowed to stand at 4° C. overnight. After the plate was washed twice with PBS-T (NaCl 29.2 g, KCl 0.2 g, $KH_2PO_4$ 0.2 g, $Na_2HPO_4$ 1.45 g, Tween-20 0.5 ml, distilled water 1 liter), 120 μl of a blocking buffer [bovine serum albumin (BSA) 5 g, thimerosal 0.05 g, NaCl 29.2 g, KCl 0.2 g, $KH_2PO_4$ 0.2 g, $Na_2HPO_4$ 1.45 g, distilled water 1 liter] was added thereto and the plate was allowed to stand at 4° C. overnight. This microtiter plate can be used as a solid phase for assay for an anti-pre-S2 antibody.

iii) Preparation of Biotinated Synthetic Pre-S2 Peptide 0.1 ml of a solution prepared by dissolving 3 mg of biotin-N-Hydroxysuccinimide ester (Polyscience Inc.) in 1 ml of N,N-dimethylformamide was added to a solution prepared by dissolving 935 μg of the synthetic pre-S2 peptide described in Reference Example 1 in 1 ml of 0.1 M $NaHCO_3$ and the mixture was allowed to stand at room temperature for 2 hours, whereby biotin was introduced to the N-terminal side of the synthetic pre-S2 peptide. In order to remove unreacted biotin, the mixture was applied on a Sephadex G-25 column (1.6 cm×80 cm) equilibrated with 0.1 M sodium phosphate buffer (pH 6.8), and a biotinated synthetic pre-S2 peptide eluted near the void volume was collected. This biotinated synthetic pre-S2 peptide can be rapidly bound to an avidinated horseradish peroxidase (HRP) to form a synthetic pre-S2 peptide labeled with HRP.

iv) Assay

30 μl of a specimen was added to 200 μl of a liquid-phase reaction mixture [40000-fold dilution of the biotinated synthetic pre-S2 peptide, 16000-fold dilution of an avidinated HRP (HRP-avidin D, Vector Inc.), 3% fetal calf serum (FCS), 0.005% thimerosal, PBS-T], and the mixture was reacted at 37° C. for 3 hours. Then, 100 μl of the reaction mixture was transferred to the solid phase (the microtiter plate coated with an anti-pre-S2 antibody) prepared in ii), and further reacted at 37° C. for 3 hours. Each well was washed with PBS-T 4 times, and 100 μl of a HRP substrate solution [24.3 mM citric acid, 51.4 mM $Na_2HPO_4$ (pH 5.0), 0.04% o-phenylenediamine, 0.0013% $H_2O_2$] was added thereto, and then the reaction was conducted at room temperature for 30 minutes. Thereafter, 100 μl of 2N $H_2SO_4$ was added thereto to terminate the reaction, and $A_{492}$ was measured by Titertek Multiskan MC (Flow Laboratories). If an anti-pre-S2 antibody is present in the specimen, the color development is suppressed according to the amount of the antibody. Therefore, the amount of an anti-pre-S2 antibody can be determined by measuring the $A_{492}$ value (inhibition ratio) of the specimen, compared with the $A_{492}$ value of the normal sample. The procedure of the inhibition method is shown in FIG. 1 (1). The amount of an anti-pre-S2 antibody contained in HB Globulin-Nichiyaku (Nippon Seiyaku Co.), an immunoglobulin preparation, was 95%, when shown by inhibition ratio. An anti-pre-S2 antibody in human sera was determined by this method. The results are shown in Table 1.

EXAMPLE 2

Assay for anti-Pre-S1 Antibody by Inhibition Method i) Preparation of Anti-Pre-S1 Antibody 1 mg of the synthetic pre-S1 peptide described in Reference Example 2 and 5 mg of keyhole limpet hemocyanin were dissolved in 2 ml of 0.2M sodium phosphate buffer (pH 7.3), and 200 μl of 2.5% glutaraldehyde was added thereto. The reaction was conducted at 4° C. for 3 hours, and then the reaction mixture was dialyzed against distilled water in a dialyzing tube to remove glutaraldehyde. A conjugate in which the synthetic pre-S1 peptide was covalently bound to keyhole limpet hemocyanin was obtained by this operation. Using this conjugate as an immunogen, three rabbits were immunized by the method described in Example 1, i). The amount of inoculation was 100 μg per rabbit for every inoculation. After 1 week from the third inoculation, the blood was collected, and 85 mg of the IgG fraction was obtained by the method described in Example 1, i). This IgG fraction contained a large amount of antibody to the pre-S1 peptide.

ii) Preparation of Solid Phase

Using the IgG fraction described above, a solid phase (microtiter plate) coated with an anti-pre-S1 antibody was prepared by the method described in Example 1, ii). This microtiter plate can be used as a solid phase for an assay for an anti-pre-S1 antibody.

iii) Preparation of Biotinated Synthetic Pre-S1 Peptide

Using 1 mg of the synthetic pre-S1 peptide described in Reference Example 2, a biotinated synthetic pre-S1 peptide was prepared according to the method described in Example 1, iii). This biotinated synthetic pre-S1 peptide can be rapidly bound to avidinated HRP to form a synthetic pre-S1 peptide labeled with HRP.

iv) Assay

Using the solid phase (microtiter plate) described in ii) and the biotinated pre-S1 peptide described in iii), an anti-pre-S1 antibody was assayed according to the method described in Example 1, iv). The titer of an anti-pre-Sl antibody contained in HB Globulin-Nichiyaku, an immunoglobulin preparation, was 92%, when shown by inhibition ratio.

An anti-pre-S1 antibody in human sera was assayed by this method. The results are shown in Table 2.

EXAMPLE 3

Assay for Anti-Pre-S2 Antibody by Sandwich Method i) Preparation of Solid Phase

500 μg of the synthetic pre-S2 peptide described in Reference Example 1 and 750 μg of thyroglobulin were dissolved in 0.2 M sodium phosphate buffer (pH 7.3), and 200 μl of 2.5% glutaraldehyde was added thereto. The reaction was conducted at 4° C. for 3 hours, and the reaction mixture was dialyzed against distilled water to remove glutaraldehyde. A conjugate in which the synthetic pre-S2 peptide was covalently bound to thyroglobulin was obtained by this operation. Using this conjugate solution [20 μg of conjugate, 0.1 M sodium carbonate buffer (pH 9.6)], a solid phase (microtiter plate) coated with this conjugate was prepared according to the method described in Example 1, ii).

ii) Assay

100 μl of the specimen or a diluted specimen with a diluent (3% FCS, 0.005% thimerosal, PBS-T) was placed in a well of the solid phase prepared in i), and the reaction was conducted at room temperature overnight. After the well was washed 4 times with PBS-T, 100 μl of a secondary antigen solution (10000-fold dilution of the biotinated synthetic pre-S2 peptide, 4000-fold dilution of an avidinated HRP, 3% FCS, 0.005% thimerosal, PBS-T) was added thereto, and the mixture was reacted at 37° C. for 2 hours. After the well was washed 4 times with PBS-T, 100 μl of a HRP substrate solution was added thereto and the reaction was conducted at room temperature for 30 minutes. Then, 100 μl of 2N $H_2SO_4$ was added thereto to terminate the reaction, and $A_{492}$ was measured. The procedure of the sandwich method is shown in FIG. 1 (2). When an anti-pre-S2 antibody was assayed by this method, the value of the normal human serum was 0.15, and the value of HB Globulin-Nichiyaku was 0.32.

EXAMPLE 4

Assay for Anti-Pre-S1 Antibody by Sandwich Method i) Preparation of Solid Phase

500 μg of the synthetic pre-S1 peptide described in Reference Example 2 and 750 μg of thyroglobulin were dissolved in 0.2 M sodium phosphate buffer (pH 7.3), and a conjugate in which the synthetic pre-S1 peptide was covalently bound to thyroglobulin was prepared by the method described in Example 3, i). Then, a solid phase (microtiter plate) coated with this conjugate was prepared according to the method described in Example 1, ii).

ii) Assay

Using the solid phase prepared in i), an anti-pre-S1 antibody was assayed in a similar manner as described in Example 3, ii). As the secondary antigen solution, there was used a solution comprising a 10000-fold dilution of the biotinated synthetic pre-S1 peptide, a 4000-fold dilution of an avidinated HRP, 3% FCS, 0.005% thimerosal and PBS-T. When the value of the normal serum was 0.1, the value of HB Globulin-Nichiyaku was 0.35.

EXAMPLE 5

Assay for Anti-Pre-S2 Antibody by Using Protein A or Anti-Human IgG Antibody to Solid Phase i) Preparation of Solid Phase

Using a Protein A solution [25 μg/ml Protein A(-Sigma Inc.), 0.1 M sodium carbonate buffer (pH 9.6)] or an anti-human IgG antibody solution [25 μg/ml anti-human IgG antibody (Kirkegaard & Perry Laboratories, Inc.), 0.1 M sodium carbonate buffer (pH 9.6)], a solid phase (microtiter plate) was coated with Protein A or an anti-human IgG antibody according to the method described in Example 1, ii).

ii) Assay

Using the solid phase prepared in i), an anti-pre-S2 antibody was assayed in a similar manner as described in Example 3, ii). The procedure of this method is shown in FIG. 1 (3). When the value of the normal serum was 0.1, the value of HB Globulin-Nichiyaku was 0.35 (Protein A).

EXAMPLE 6

Assay for Anti-Pre-S1 Antibody by Using Protein A or Anti-Human IgG Antibody to Solid Phase i) Assay

Using the solid phase prepared in Example 5, i), an anti-pre-S1 antibody was assayed in a similar manner as described in Example 4, ii).

When the value of the normal serum was 0.08, the value of HB Globulin-Nichiyaku was 0.41 (Protein A).

EXAMPLE 7

Assay for Anti-Pre-S2 Antibody by Competitive Method i) Preparation of Biotinated Anti-Pre-S2 Antibody

Using 1 mg of the IgG fraction containing anti-pre-S2 antibody described in Example 1, i), a biotinated anti-pre-S2 antibody was prepared according to the method described in Example 1, iii). This biotinated anti-pre-S2 antibody can be rapidly bound to avidinated HRP to form anti-pre-S2 antibody labeled with HRP.

ii) Assay

30 μl of a specimen was added to 200 μl of a reaction mixture [40000-fold dilution of the biotinated anti-pre-S2 antibody, 16000-fold dilution of an avidinated HRP, 3% FCS, 0.005% thimerosal, PBS-T], and immediately 100 μl of the resulting mixture was dividedly poured into each well of the solid phase coated with the conjugate of synthetic pre-S2 peptide and thyroglobulin prepared in Example 3, i), the reaction was conducted at 37° C. for 3 hours. After the well was washed 4 times with PBS-T, 100 μl of a HRP substrate solution was added thereto and the reaction was conducted at room temperature for 30 minutes. Then, 100 μl of 2N $H_2SO_4$ was added thereto to terminate the reaction, and $A_{492}$ was measured. If an anti-pre-S2 antibody is present in the specimen, the color development is suppressed according to the amount of the antibody. Therefore, the amount of anti-pre-S2 antibody can be determined by assaying the inhibition ratio of the $A_{492}$ value of the specimen, compared with the $A_{492}$ value of the normal sample. The procedure of the competitive method is shown in FIG. 1 (4). The titer of an anti-pre-S2 antibody contained in HB Globulin-Nichiyaku was 32, when expressed as the dilution which reduces the activity to 50%.

EXAMPLE 8

Assay for Anti-Pre-S1 Antibody by Competitive Method i) Preparation of Biotinated Anti-Pre-S1 Antibody

Using 1 mg of the IgG fraction containing an anti-pre-S1 antibody described in Example 2, i), a biotinated anti-pre-S1 antibody was obtained according to the method described in Example 1, iii). This biotinated anti-pre-S1 antibody can be rapidly bound to an avidinated HRP to form an anti-pre-S1 antibody labeled with HRP.

ii) Assay

Anti-pre-S1 antibody was assayed according to the method described in Example 7, ii). As the reaction solution, there was used a solution comprising a 40000-fold dilution of the biotinated anti-pre-S1 antibody, a 16000-fold dilution of an avidinated HRP, 3% FCS, 0.005% thimerosal and PBS-T. The titer of anti-pre-S2 antibody contained in HB Globulin-Nichiyaku was 64, when expressed as the dilution which inhibits the activity to 50%.

TABLE 1

| Detection of anti-pre-S2 antibody in Human sera | |
|---|---|
| Specimen | Inhibition ratio (%)* |
| Healthy human sera negative for anti-HBs antibody | |
| A | 3.4 |
| B | 5.5 |
| C | 2.0 |
| Human sera positive for anti-HBs antibody | |
| D | 45.0 |
| E | 82.5 |
| F | 85.2 |

*The value of the diluent was taken as the inhibition ratio of 0%, and the value obtained when biotinated pre-S2 peptide was removed from the reaction system was taken as the inhibition ratio of 100%.

TABLE 2

| Detection of anti-pre-S1 antibody in human sera | |
|---|---|
| Specimen | Inhibition ratio (%)* |
| Healthy human sera negative for anti-HBs antibody | |
| G | 1.0 |
| H | 1.3 |
| I | 3.7 |
| Human sera positive for anti-HBs antibody | |
| J | 51.8 |
| K | 76.1 |
| L | 72.0 |

*The value of the diluent was taken as the inhibition ratio of 0%, and the value obtained when biotinated pre-S1 peptide was removed from the reaction system was taken as the inhibition ratio of 100%.

The following references, which are referred to for their disclosures at various points in this application, are incorporated herein by reference.

Nature 315, 154 (1985)
Vaccine, 4, 35 (1986)
Proc. Natl. Acad. Sci. U.S.A., 83, 9174 (1986)
Cell, 46, 429 (1986)
Hepatology, 6, 360 (1986)
Hepatology, 6, 354 (1986)
Proc. Natl. Acad. Sci. U.S.A., 81, 7708 (1984)

Gene, 40, 23 (1985)
Biochem. Biophys. Res. Comm. 141, 942 (1986)
Gene, 48, 155 (1986)
Japanese Patent Application No. 193833/1986.

We claim:

1. An assay for an anti-pre-S2 antibody in a human serum specimen which comprises reacting a human serum specimen, a biotinated pre-S2 peptide having the amino acid sequence:

FHQALLDPRVRGLYFPAGGSSSGTVNP and an avidinated enzyme with an anti-pre-S2 antibody which is bound to a carrier, and measuring enzyme activity on the carrier wherein the amount of measured enzyme activity is inversely proportional to the amount of pre S-2 antibody in the specimen.

2. The assay as claimed in claim 1, wherein the enzyme is horseradish peroxidase.

3. The assay as claimed in claim 1, wherein the carrier is a particle or a plate.

4. An assay for an anti-pre-S2 antibody in a human serum specimen which comprises reacting a human serum specimen with a pre-S2 peptide having the amino acid sequence:

FHQALLDPRVRGLYFPAGGSSSGTVNP which is bound to a carrier, then adding a biotinated pre-S2 peptide having the amino acid sequence:

FHQALLDPRVRGLYFPAGGSSSGTVNP and an avidinated enzyme thereto, and measuring enzyme activity on the carrier wherein the amount of measured enzyme activity is proportional to the amount of pre S-2 antibody in the specimen.

5. The assay as claimed in claim 4, wherein the enzyme is horseradish peroxidase.

6. The assay as claimed in claim 4, wherein the carrier is a particle or a plate.

7. An assay for an anti-pre-S2 antibody in a human serum specimen which comprises reacting a human serum specimen, a biotinated anti-pre-S2 antibody and an avidinated enzyme with a pre-S2 peptide having the amino acid sequence:

FHQALLDPRVRGLYFPAGGSSSGTVNP which is bound to a carrier, and measuring enzyme activity on the carrier wherein the amount of measured enzyme activity is inversely proportional to the amount of pre S-2 antibody in the specimen.

8. The assay as claimed in claim 7, wherein the enzyme is horseradish peroxidase.

9. The assay as claimed in claim 7, wherein the carrier is a particle or a plate.

10. An assay for an anti-pre-S2 antibody in a human serum specimen which comprises reacting a human serum specimen, a biotinated pre-S2 peptide having the amino acid sequence:

FHQALLDPRVRGLYFPAGGSSSGTVNP and an avidinated enzyme with an anti-human immunoglobulin G antibody or Protein A which is bound to a carrier, and measuring enzyme activity on the carrier wherein the amount of measured enzyme activity is proportional to the amount of pre S-2 antibody in the specimen.

11. The assay as claimed in claim 10, wherein the enzyme is horseradish peroxidase.

12. The assay as claimed in claim 10, wherein the carrier is a particle or a plate.

* * * * *